(12) United States Patent
Wang et al.

(10) Patent No.: US 6,558,900 B2
(45) Date of Patent: May 6, 2003

(54) REGULATION OF APOPTOSIS AND IN VITRO MODEL FOR STUDIES THEREOF

(75) Inventors: Xiaodong Wang; Xuesong Liu, both of Dallas, TX (US)

(73) Assignee: Emory University, Atlanta, GA (US)

( * ) Notice: Subject to any disclaimer, the term of this patent is extended or adjusted under 35 U.S.C. 154(b) by 6 days.

(21) Appl. No.: 08/891,525

(22) Filed: Jul. 11, 1997

(65) Prior Publication Data

US 2002/0081643 A1 Jun. 27, 2002

Related U.S. Application Data

(60) Provisional application No. 60/021,268, filed on Jul. 12, 1996.

(51) Int. Cl.[7] .............................. C12Q 1/68; C12Q 1/37; G01N 33/53; G01N 33/573

(52) U.S. Cl. ........................... 435/6; 435/7.1; 435/7.23; 435/7.4; 435/7.92; 435/23; 436/63; 436/64

(58) Field of Search ......................... 435/6, 7.1, 7.23, 435/7.4, 7.92, 23; 436/63, 64

(56) References Cited

U.S. PATENT DOCUMENTS

| | | | |
|---|---|---|---|
| 5,550,019 A | 8/1996 | Reed ............................. | 435/6 |
| 5,672,500 A | * 9/1997 | Litwack et al. .......... | 435/240.2 |

OTHER PUBLICATIONS

Wang et al. "Cleavage of sterol regulatory element binding proteins (SREBPs) by CPP32 during apoptosis" The EMBO Journal. vol. 15. No. 5, pp. 1012–1020, Mar. 1996.*
Darnell et al. "Molecular Cell Biology" p. 159, 1986.*
Benveniste, P. and Cohen, A., "p53 expression is required for thymocyte apoptosis induced by adenosine deaminase deficiency," (1995) *Proc. Natl. Acad. Sci. USA* 92:8373–8377.
Casciola–Rosen, L.A. et al., "Specific Cleavage of the 70–kDa Protein Component of the U1 Small Nuclear Ribonucleoprotein Is a Characteristic Biochemical Feature of Apoptotic Cell Death," (1994) *J. Biological Chemistry* 269(49):30757–30760.
Cherney, B.W. et al., "cDNA sequence, protein structure, and chromosomal location of the human gene for poly(ADP–ribose) polymerase," (1987) *Proc. Natl. Acad. Sci. USA* 84:8370–8374.
Cohen, A. et al., "Deoxyadenosine triphosphate as a potentially toxic metabolite in adenosine deaminase deficiency," (1978) *Proc. Natl. Acad. Sci. USA* 75(1):472–476.
Duan, H. et al., "ICE–LAP3, a Novel Mammalian Homologue of the *Caenorhabditis elegans* Cell Death Protein Ced–3 Is Activated during Fas–and Tumor Necrosis Factor–induced Apoptosis," (1996) *J. Biological Chemistry* 271(3):1621–1625.

Enari, M. et al., "Apoptosis by a cytocolic extract from Fas–activated cells," (1995) *The EMBO Journal* 14(21):5201–5208.
Fernandes–Alnemri, T. et al., "CPP32, a Novel Human Apoptotic Protein with Homology to *Caenorhabditis elegans* Cell Death Protein Ced–3 and Mammalian Interleukin–1β–converting Enzyme," (1994) *J. Biological Chemistry* 269(49):30761–30764.
Goday, A. et al., "Human B Lymphocytes and Thymocytes but Not Peripheral Blood Mononuclear Cells Accumulate High dATP Levels in Conditions Simulating ADA Deficiency," (1998) *Biochemical Pharmacology* 34(19):3561–3569.
Gonzales, D.H. and Neupert, W., "Biogenesis of Mitochondrial c–Type Cytochromes," (1990) *J. Bioenergetics and Biomembranes* 22(6):753–768.
Hua, X. et al., "SREBP–2, a second basic–helix––loop–helix– leucine zipper protein that stimulates transcription by binding to a sterol regulatory element," (1993) *Proc. Natl. Acad. Sci. USA* 90:11603–11607.
Jemmerson, R. et al., "A monoclonal antibody specific for a cytochrome c T cell stimulatory peptide inhibits T cels responses and affects the way the peptide associates with antigen–presenting cells," (1991) *Eur. J. Immunol.* 21:143–151.
Jemmerson, Ronald and Johnson, J.G., "Different functional boundaries for the major antigenic region of two cytochromes c," (1991) *Proc. Natl. Acad. Sci. USA* 88:4428–4432.
Martin, S.J. et al., "Cell–free reconstitution of Fas–, UV radiation–and ceramide–induced apoptosis," (1995) *The EMBO Journal* 14(21):5191–5200.
Nicholson, D.W. et al., "Identification and inhibition of the ICE/CED–3 protease necessary for mammalian apoptosis," (1995) *Nature* 376:37–43.
Rüegg, U.T. and Burgess, G.M., "Staurosporine, K–252 and UCN–01: potent but nonspecific inhibitors of protein kinases," (1989) *TiPS* 10:218–220.

(List continued on next page.)

*Primary Examiner*—Geetha P. Bansal
(74) *Attorney, Agent, or Firm*—Greenlee Winner and Sullivan, PC

(57) ABSTRACT

A cell-free system based on the cytosol of normally growing cells, which reproduces measurable aspects of the apoptotic program, is provided. The apoptotic program is initiated by addition of DATP in the specific exemplification of the HeLa 100,000×g supernatant. Fractionation of the cytosol yielded a 15 kDa protein, identified by absorption spectrum and protein sequence as cytochrome c, that is required for in vitro apoptosis. Elimination of cytochrome c from cytosol by immunodepletion or inclusion of sucrose to stabilize mitochondria during cytosol preparation, diminished the apoptotic activity. Addition of exogenous cytochrome c to cytochrome c-depleted extracts restored apoptotic activity. Cells undergoing apoptosis in vivo showed increased release of cytochrome c to their cytosol, suggesting that mitochondria may function in apoptosis by releasing cytochrome c.

22 Claims, 12 Drawing Sheets

OTHER PUBLICATIONS

Schlegel, J. et al., "CPP32/Apopain Is a Key Interleukin 1β Converting Enzyme–like Protease Involved in Fas–mediated Apoptosis," (1996) *J. Biological Chemistry* 271(4):1841–1844.

Tewari, M. et al., "Yama/CPP32β, a Mammalian Homolog of CED–3, Is a CrmA–Inhibitable Protease That Cleaves the Death Substrate Poly(ADP–Ribose) Polymerase," (1995) *Cell* 81:801–809.

Wakade, A.R. et al., "Deoxynucleoside Induces Neuronal Apoptosis Independent of Neurotrophic Factors," (1995) *J. Biological Chemistry* 270(30):17986–17992.

Wang, X. et al., "Nuclear Protein That Binds Sterol Regulatory Element of Low Density Lipoprotein Receptor Promoter," (1993) *J. Biological Chemistry* 268(19):14497–14504.

Wang, X. et al., "Purification of an Interleukin–1β Converting Enzyme–related Cysteine Protease That Cleaves Sterol Regulatory Element–binding Proteins between the Leucine Zipper and Transmembrane Domains," (1995) *J. Biological Chemistry* 270(30):18044–18050.

Wyllie, A. H., "Glucocorticoid–induced thymocyte apoptosis is associated with endogenous endonuclease activation," (1980) *Nature* 284:555–556.

Yuan, Junying and Horvitz, H. Robert, "The *Caenorhabditis elegans* Genes ced–3 and ced–4 Act Cell Autonomously to Cause Programmed Cell Death," (1990) *Developmental Biology* 138:33–41.

Yuan, J. et al., "The C. elegans Cell Death Gene ced–3 Encodes a Potent Similar to Mammalian Interleukin–1β–Converting Enzyme," (1993) *Cell* 75:641–652.

Bertrand, et al. "Detection of Apoptosis–Associated DNA Fragmentation Using a Rapid and Quantitative Filter Elution Assay"; (1995) *Drug Development Research* 34:138–144.

Bertrand, et al. "Induction of a Common Pathway of Apoptosis by Staurosporine"; (1994) *Experimental Cell Research* 211:314–321.

* cited by examiner

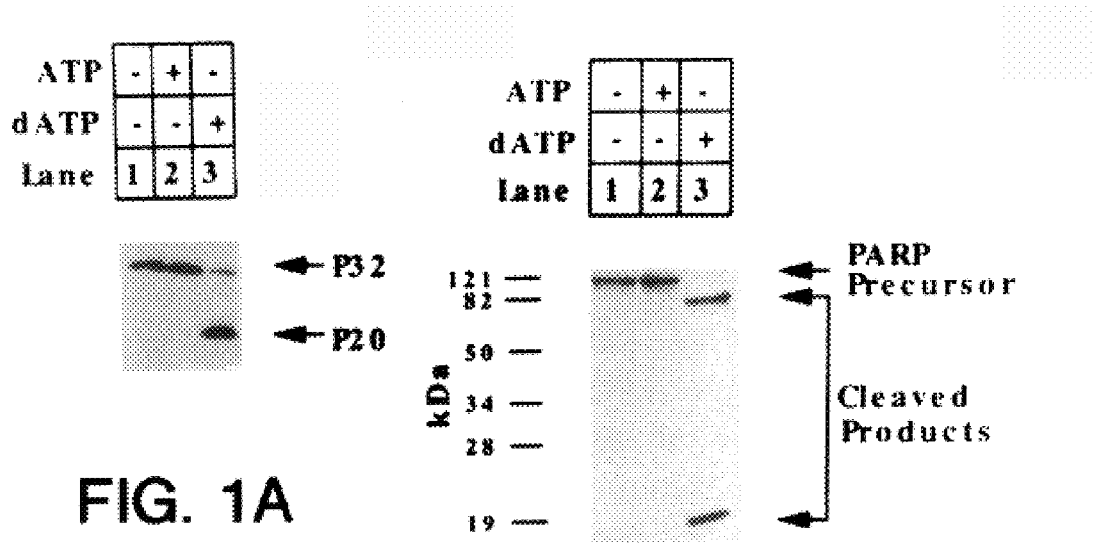
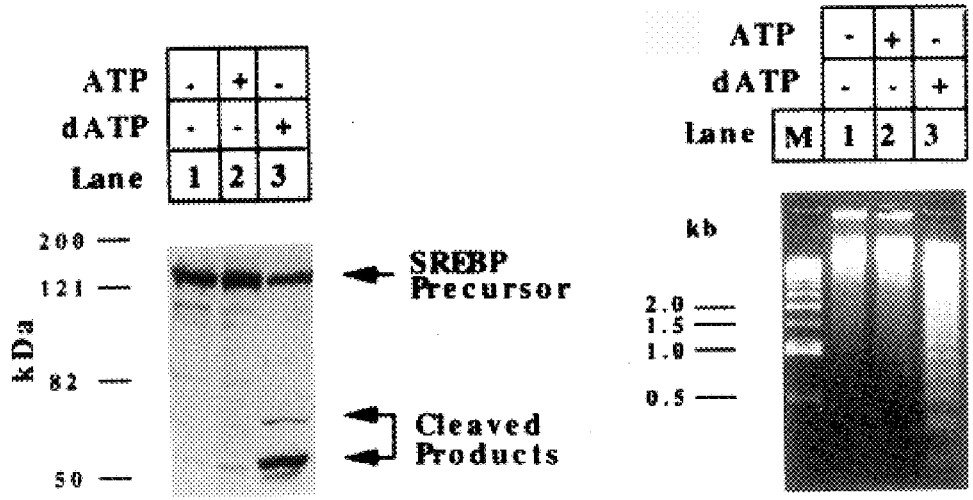
FIG. 1A
FIG. 1B
FIG. 1C
FIG. 1D

REGULATION OF APOPTOSIS AND IN VITRO MODEL FOR STUDIES THEREOF

CROSS REFERENCE TO RELATED APPLICATIONS

This application is a continuation in Part of U.S. Provisional Patent application No. 60/021,268, filed Jul. 12, 1996.

ACKNOWLEDGEMENT OF FEDERAL RESEARCH SUPPORT

Not applicable.

BACKGROUND OF THE INVENTION

The field of this invention is the area of apoptosis (programmed cell death) and methods for the study of the regulation thereof. Specifically, the present invention provides an in vitro system for the analysis of apoptosis and specific regulators of the apoptotic pathway.

Apoptosis is a distinct form of cell death controlled by an internally encoded suicide program [reviewed by Steller, H. (1995) Science 267, 1445–1449; White, E. (1996) Gene & Dev. 10, 1–15]. Morphologic changes associated with apoptosis include condensation of nucleoplasm and cytoplasm, blebbing of cytoplasmic membranes, and fragmentation of the cell into apoptotic bodies that are rapidly phagocytosed by neighboring cells [Kerr, J. (1971) J. Pathol. 105, 13–20; Wyllie et al. (1980) Int. Rev. Cytol. 68, 251–305]. Biochemical markers of apoptosis include DNA fragmentation into nucleosomal fragments [Wyllie, A. (1980) Nature 284, 555–556], activation of the interleukin lb converting enzyme (ICE)-family of proteases [Duan et al. (1996) J. Biol. Chem. 271, 1621–1625; Wang et al. (1996) EMBO J. 15, 1012–1020], and cleavage of substrates of the ICE-family of proteases, including poly(ADP-ribose) polymerase (PARP) [Tewari et al. (1995) Cell 81, 801–809; Nicholson et al. (1995) Nature 376, 37–43] sterol regulatory element binding proteins (SREBPs) [Wang et al. (1995) J. Biol. Chem. 270, 18044–18050; Wang et al. 1996, supra], nuclear lamin [Lazebnik et al. (1995) Proc. Natl. Acad. Sci. USA 92, 9042–9046], and the U1 associated 70 kDa protein [Casciola-Rosen et al. (1994) J. Biol. Chem. 269, 30757–30760].

The cell suicide program is illustrated by genetic studies in the nematode Caenorhabditis elegans [Hengartner and Horvitz (1994) Philos. Trans. R. Soc. London Ser. B 345, 243–246]. Two genes involved in the control of programmed cell death in C. elegans have been well characterized. One gene (ced-9) encodes a protein that prevents cells from undergoing apoptosis [Hengartner et al. (1992) Nature 356, 494–499], and the ced-3 gene encodes a protease required for initiation of apoptosis [Yuan and Horvitz (1990) Dev. Biol. 138, 33–41].

The bcl-2 family of genes are mammalian counterparts of ced-9 [Hengartner and Horvitz (1994) Cell 76, 665–676]. Over-expression of bcl-2 coding sequences prevents mammalian cells from undergoing apoptosis in response to a variety of stimuli [reviewed by Reed, J. C. (1994) J. Cell Biol. 124, 1–6]. The BCL-2 protein is located primarily on the outer membranes of mitochondria [Monaghan et al. (1992) J. Hist. Cytochem. 40, 1819–1825; Krajewski et al. (1993) Cancer Res. 53, 4701–4714; de Jong et al. (1994) Cancer Res. 54, 256–260]. The presence of BCL-2 on the mitochondria surface is correlated with a block in the release of cytochrome c in response to triggers of apoptosis in cells which do not express the BCL-2 protein on the mitochondrial surface [Yang et al. (1997) Science 275, 1129–1132]. Holocytochrome c, but not apocytochrome c, triggers activation of CPP32 and the apoptotic cascade. Without wishing to be bound by theory, it is believed that the Bcl-2 protein inhibits apoptosis by preventing release of holocytochrome c from the mitochondrial membrane and also prevents depolarization of the mitochondrial membrane.

The CED-3 protein is a cysteine protease related to the ICE-family of proteases in mammalian cells [Yuan et al. (1993) Cell 75, 641–652]. The closest mammalian homolog of CED-3 is CPP32 [Fernandes-Alnemri et al. (1994) J. Biol. Chem. 269, 30761–30764], which cleaves PARP and SREBPs in cells undergoing apoptosis [Tewari et al. (1995) supra; Nicholson et al. (1995) supra; Wang et al. (1996) supra]. CPP32, which is also called caspase-3, is closely related to CED-3 in terms of amino acid sequence identity and substrate specificity [Xue and Horvitz (1995) Nature 377, 248–251]. Like CED-3 in C. elegans, CPP32 normally exists in the cytosolic fraction as an inactive precursor; that precursor is activated proteolytically in cells undergoing apoptosis [Schlegel et al. (1996) J. Biol. Chem. 271, 1841–1844, 1996; Wang et al. (1996) supra]. Further evidence for the requirement for active CPP32 in apoptosis is that a tetrapeptide aldehyde inhibitor that specifically inhibits CPP32 activity blocks the ability of cytosol from apoptotic cells to induce apoptosis-like changes in normal nuclei in vitro. [Nicholson et al. (1995) supra].

Triggering of apoptosis by activated CPP32 is part of the highly regulated mechanism for initiation of apoptosis; careful regulation of this pathway is necessary to prevent unwanted cell death. CPP32 is activated by multiple proteolytic cleavages of its 32 kDa precursor form, generating the 17/11 kDa or 20/11 kDa active form [Nicholson et al. (1995) supra; Wang et al. (1995) supra]. CPP32 is activated by cleavage at aspartic acid residues, a hallmark of ICE-like proteases [Thomberry et al. (1992) Nature 356, 768–774], and a cascade of ICE-like proteolytic cleavages leading to apoptosis has been proposed [Tewari et al. (1995) supra; Wang et al. (1996) supra]. Activated CPP32 from HeLa cell extracts cleaves the CPP32 precursor [Wang et al. (1996) supra], indicating that CPP32 can be activated through autocatalysis. Autocatalytic cleavage is probably responsible for active enzyme when the CPP32 precursor is expressed in large quantity in bacteria [Xue and Horvitz (1995) supra]. Recently, another ICE-family protease has been identified that may be responsible for cleaving the CPP32 precursor into the 20/11 kDa active form. This enzyme has been purified from hamster liver extracts and identified as the hamster homolog of Mch2a [Liu et al. (1996) J. Biol. Chem. 271, 13371–13376; Fernandes-Alnemri et al. (1995) Cancer Res. 55, 2737–2742]. Autocatalysis and the protease cascade may provide the signal amplification necessary for rapid and irreversible apoptosis, but the intracellular factors that trigger this amplification have yet to be identified.

There have been several previous reports of cell-free apoptosis systems that induce apoptotic changes in the added nuclei [Lazebnik et al. (1993) J. Cell Biol. 123, 7–22; Newmeyer et al. (1994) Cell 79, 353–364; Eeari et al. (1995) EMBO. J. 14, 5201–5208; Martin et al. (1995) EMBO J. 14, 5191–5200]. These systems require cytosol from cells that are already undergoing apoptosis in vivo; thus, they cannot be used to detect triggering factors.

There is a need in the art for in vitro methods for the analysis of compounds and biological factors which trigger or accelerate apoptosis or which interfere with the induction of apoptosis, as well as those which can increase the apoptotic effect of chemotherapeutic agents in cancers, especially those expressing oncogenic bcl-2. This need is met by the present invention, which allows the study of apoptosis and regulators thereof in a cell-free system in which the analysis is not complicated by previous induction of the apoptotic pathway in the cells used to prepare the test extracts.

SUMMARY OF THE INVENTION

The present invention provides an in vitro system and methods for the analysis of the regulation of apoptosis and for the identification of activators and inhibitors of the apoptotic pathway; the present system is improved over prior art systems for the study of apoptosis in that the prior art systems depended on cell free extracts prepared from organisms in which the apoptosis pathway had already been induced. Thus, the present system and methods permit freedom from the potential interference of apoptosis-inducing factors or other conditions on which prior art systems have relied.

As exemplified herein, the present invention provides an in vitro system for analysis of apoptosis and its regulation, where the test system includes a 100,000×g supernatant of HeLa cells from suspension culture (S-100). In its first aspect, the HeLa S-100, to which challenge compounds are added, is assayed for CPP32 proteolytic activity using radiolabeled poly(adenosine diphosphate-ribose polymerase (PARP) and radiolabeled sterol regulatory binding protein 2 (SREBP-2) and sodium dodecyl sulfate polyacrylamide gel electrophoresis (SDS-PAGE) and autoradiography. The radiolabeled PARP and SREBP-2 can be prepared by in vitro translation in the presence of $^{35}$S-methionine as described in Example 3 herein. In a second aspect, the HeLa S-100, to which challenge compounds are added, is assayed for DNA fragmentation activity, by incubating the treated S-100 with hamster liver cell nuclei and then extracting the genomic DNA and analyzing by agarose gel electrophoresis. The specific proteolytic activity is accelerated by the addition of dATP or dADP (at a concentration from about 0.1 to about 2 mM, preferably about 1 mM.) DNA fragmenting activity is similarly dependent on the presence of dATP. It has been demonstrated that cytochrome c is required in the cell-free extract for the dATP-dependent activation of the apoptotic pathway, especially for the activation of the apoptosis marker protease.

The present invention provides a cell-free system which duplicates the features of the apoptotic program, including the activation of CPP32 and DNA fragmentation. Apoptosis in this system is initiated by the presence of soluble cytochrome c and dATP at sufficient concentrations. This system allows the fractionation and purification of the biochemical components that trigger the activation of the apoptotic proteases and DNA fragmentation.

The present invention further provides a method for identifying antagonists of dATP in the cytosol of adenosine deaminase-deficient cells, such as T cells from persons with severe combined immunodeficiency. dATP levels in adenosine deaminase-deficient cells are elevated in comparison to those of normal cells, and without wishing to be bound by any particularly, this is believed to contribute to the symptoms of the deficiency. Identification of antagonists of the initiation of apoptosis can lead to treatments for the amelioration of the clinical state of deficient individuals.

The present invention also provides methods for identification of compounds which trigger apoptosis even where the bcl-2 oncogene protein is present. The bcl-2 oncogene is associated with resistance to chemotherapy in human cancer, and compounds which cause CPP32 protease and DNA fragmentation nuclease-activation in bcl-2 oncogene extracts can be identified in the cell free assays of the present invention where the S-100 extract is prepared from BCL-2 expressing cells.

Additionally, the present invention allows the identification of compounds which effectively increase the apoptotic response to dATP and/or cytochrome c, including those which increase dATP levels in treated cells and -those which promote release of cytochrome c from mitochondrial membranes. Such compounds can be used to increase the effectiveness of chemotherapeutic agents which act by inducing apoptosis.

BRIEF DESCRIPTION OF THE DRAWINGS

FIGS. 1A–1D illustrate dATP-dependent activation of CPP32 and DNA fragmentation in vitro. Aliquots (10 µl) of HeLa cell S-100 (50 µg) were incubated alone (lane 1), in the presence of 1 mM ATP (lane 2), or in the presence of 1 mM dATP (lane 3) at 30° C. for 1 hr in a final volume of 20 µl of buffer A. FIG. 1A, samples were subjected to SDS-PAGE and transferred to a nitrocellulose filter, probed with a monoclonal anti-CPP32 antibody, and the antigen/antibody complex was visualized by the ECL method. The filter was exposed to Kodak X-OMAT AR X-ray film for 1 min. In FIG. 1B, an aliquot of 10 µl of in vitro translated, $^{35}$S-labeled PARP was added to each reaction. After 5 min, the samples were subjected to SDS-PAGE and transferred to a nitrocellulose filter. The filter was exposed to film for 2 hr at room temperature. In FIG. 1C, a 5 µl aliquot of in vitro translated, $^{35}$S-labeled SREBP-2 was added to each reaction. After incubation at 30° C. for 30 min, the samples were subjected to SDS-PAGE, the gel was dried and exposed to film for 2 hr at room temperature. In FIG. 1D, a 50 µl aliquot of HeLa cell S-100 (250 µg) was incubated with 6 µl Hamster Liver nuclei in the absence (lane 1), or presence of 1 mM ATP (lane 2) or dATP (lane 3) for 2 hr at 37° C. in a final volume of 60 µl of buffer A. DNA was isolated as described in the Examples and size-separated by agarose gel electrophoresis (2% agarose), and the DNA was visualized by ethidium bromide staining.

FIG. 2A shows the results of incubating a 10 µl aliquot of HeLa S-100 (50 µg) was incubated with a 3 µl aliquot of in vitro translated, $^{35}$S-labeled CPP32 at 30° C. for 1 hr in a final volume of 20 µl in the presence of 1 mM indicated nucleotide. The samples were subjected to SDS-PAGE and transferred to a nitrocellulose filter. The filter was exposed to film for 16 hours at room temperature. In FIG. 2B, a 50 µl aliquot of HeLa S-100 (250 µg) was incubated with each aliquot of 6 µl hamster liver nuclei at 37° C. for 2 hr in the presence of 1 mM indicated nucleotide. The DNA was isolated, analyzed by 2% agarose gel electrophoresis and visualized by ethidium bromide staining.

In FIG. 7A, 10 μl aliquots of HeLa S-100 (50 μg) (lanes 1 and 2), or 10 μl aliquots of HeLa S-100 immunodepleted of cytochrome c (lanes 3 and 4), or 10 μl of HeLa S-100 immunodepleted of cytochrome c supplemented with 0.2 μg Apaf-2 purified through the Mono S column (H) (lanes 5 and 6), bovine heart cytochrome c (B) (lanes 7 and 8), or rat liver cytochrome c (R) (lanes 9 and 10), were incubated with aliquots of 3 μl in vitro translated, $^{35}$S-labeled CPP32 in the absence (lanes 1, 3, 5, 7, 9) or presence (lanes 2, 4, 6, 8, 10) of 1 mM dATP at 30° C. for 1 hr in a final reaction volume of 20 μl of buffer A. Samples were subjected to SDS-PAGE and transferred to a nitrocellulose filter which were then exposed to film for 16 hr at room temperature. In FIG. 7B, HeLa S-100 (50 μg) immunodepleted of cytochrome c were reconstituted with the indicated amount of Apaf-2 (purified through Mono S column step) in a CPP32 cleavage reaction as described in FIG. 7A. The cleaved products (p20) were quantified in a Fuji-1000 phosphorimager machine and plotted in comparison with that generated by HeLa S-100. In FIG. 7C, aliquots of 50 μl of HeLa S-100 (250 μg) (lanes 1 and 2), or 50 μl of HeLa S-100 immunodepleted of cytochrome c (lanes 3 and 4), or 50 μl of HeLa S-100 immunodepleted of cytochrome c supplemented with 1 μg apaf-2 purified through the Mono S column (H) (lanes 5 and 6), bovine heart cytochrome c (B) (lanes 7 and 8), or rat liver cytochrome c (R) (lanes 9 and 10), were incubated with aliquots of 6 μl hamster liver nuclei in the absence (lanes 1, 3, 5, 7, 9) or presence (lanes 2, 4, 6, 8, 10) of 1 mM dATP at 37° C. for 2 hr in a final reaction volume of 60 μl. The DNA were isolated as described in the Examples, analyzed on 2% agarose gel electrophoresis, and the DNA was visualized by ethidium bromide staining. In FIG. 7D, DNA fragmentation assays were carried out as in FIG. 7C using HeLa S-100 immunodepleted of cytochrome c alone (a,b) or supplemented with Apaf-2 purified through Mono S column step (c,d) in the absence (a,c) or presence of 1 mM dATP (b,d). After 2 hr incubation at 37° C., an aliquot of each reaction (30 μl) was stained with 4',6'-diamidino-2-phenylindole (DAPI), and observed under a fluorescence microscope with a UV-2A combination filter.

In FIG. 10A, a 50 μg aliquot of HeLa cell S-100 as in FIGS. 1–7 (lane 1), or S-cytosol from HeLa cells (lane 2), or S-cytosol from HeLa cells treated with staurosporine for 6 hr. In lane 4, aliquot of 0.2 μg of Apaf-2 purified through Mono S column step. Proteins were separated using 15% SDS-PAGE, transferred to a nitrocellulose filter, and probed with a monoclonal anti-cytochrome c antibody and the antigen/antibody complex was visualized by the ECL method as described herein. Kodak X-OMAT AR X-ray film was exposed for 15 seconds. The arrow denotes the position of cytochrome c; X denotes protein bands cross-reacting with this antibody. In FIG. 10B, aliquots containing 4.5 μg of S-cytosol from HeLa cells (−staurosporine) or HeLa cells treated with 1 μM staurosporine for 6 hr (+staurosporine) were incubated with 10 μl aliquots of in vitro translated, 35S-labeled PARP for 30 min at 30° C. in a volume of 20 μl of buffer A. Samples were then subjected to 12% SDS-PAGE, transferred to a nitrocellulose filter, and film was exposed for 4 hr at room temperature.

DETAILED DESCRIPTION OF THE INVENTION

Figure 2A:
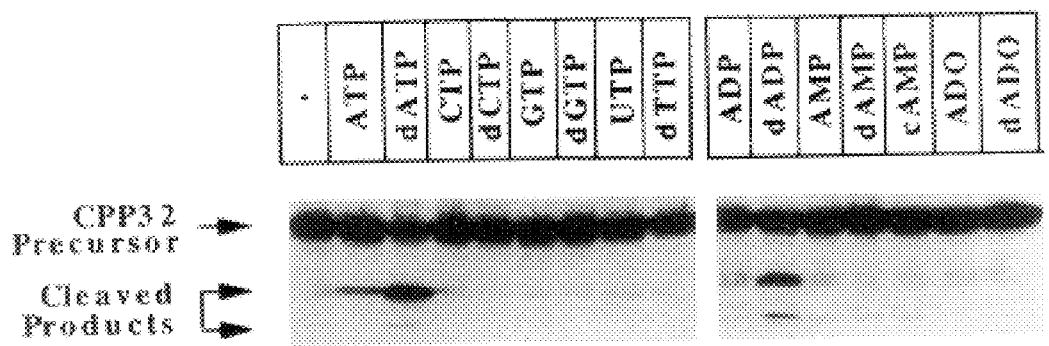
FIGS. 2A–2B illustrate the nucleotide specificity for in vitro activation of CPP32 and DNA fragmentation.

Apoptosis, or cell death, is a natural phenomenon. Modulation of normal apoptosis or activation of the apoptotic pathway in cells in which apoptosis is inhibited due to the expression of oncogenes, for example, can lead to longer and enhanced life and/or improved medical treatment methods, for example, in cancer patients.

The present invention provides a method for the identification of inducers and/or inhibitors of apoptosis in a cell-free system comprising 100,000×g supernatant of cell cytosol (S-100) prepared from actively growing cells and containing the inactive CPP32 and nuclease precursors. Desirably, the S-100 is prepared from mammalian cells, for example, HeLa cells. Activation of the apoptosis marker protease CPP32 and the marker nuclease are triggered in this system in the presence of dATP and soluble cytochrome c in a 100,000×g cytosol supernatant. Modification of the assay preparation conditions allows the identification of compounds, proteins or compositions which can substitute either for the dATP or the soluble cytochrome c or for both. Initiation of the apoptotic pathway is detected by the proteolytic cleavage of SREBPs or PARP by the CPP32 protease which is activated at an early step of the apoptotic pathway. Triggering of the apoptotic pathway can also be detected via the activation of the nuclease. Active CPP32 protease and active apoptotic DNA fragmentation nuclease are marker enzymes of the apoptotic pathway. In this system soluble cytochrome c and dATP trigger activation of the marker enzymes for apoptosis. It is understood that analogs of dATP and dADP function in triggering the apoptotic activation as well.

Compounds or proteins which inhibit the initiation of the apoptotic pathway are detected by their prevention of the activation of the CPP32 protease or the marker nuclease in the presence of cytochrome c and dATP, conditions which normally activate the pathway.

Compounds or proteins which counteract the apoptosis-inhibiting activity of the bcl-2 gene product (or of other oncogene products) can be identified by their ability to allow the activation of the marker enzymes of the apoptotic pathway even in the presence of dATP and cytochrome c in S-100 extracts of cells expressing bcl-2 or similar oncogenes. Compositions identified in the present assay system can be then used to increase the activity of chemotherapeutic agents used in the treatment of cancers and other hyperplastic disorders, especially in cells expressing oncogenic bcl-2 or other oncogenes which decrease apoptosis.

Activation of CPP32 and DNA fragmentation are two well characterized biochemical markers of apoptosis and its initiation. With the goal of producing an in vitro system that duplicates apoptosis, we prepared 100,000×g cytosolic supernatant (S-100) from suspension cultures of HeLa cells. The activation of CPP32 is the result of cleavage of its 32 kDa precursor into the 20 kDa $NH_2$-terminal fragment and 11 kDa COOH-terminal fragment [Nicholson et al. (1995) supra], thus the activation of CPP32 in the HeLa cell S-100 was monitored by Western blot analysis using a monoclonal antibody against the 20 kDa fragment of CPP32 (FIG. 1A). The enzymatic activity of CPP32 was assayed by measuring the cleavage of two $^{35}$S-labeled substrates, PARP (FIG. 1B) and SREBP-2 (FIG. 1C). DNA fragmentation was assayed by incubating the HeLa cell S-100 with nuclei isolated from hamster liver followed by genomic DNA extraction and analysis by agarose gel electrophoresis. We found that deoxyadenosine-5-triphosphate (dATP) markedly accelerated the activation of CPP32 in the HeLa cell S-100. As shown in FIGS. 1A–1B, no activation of CPP32 was observed when the HeLa cell S-100 was incubated in the presence or absence of 1 mM ATP at 30° C. for 1 hr (FIG. 1A, lanes 1 and 2). However, in the presence of 1 mM dATP, most of the CPP32 in the HeLa cell S-100 was activated (FIG. 1A, lane 3). The activated extracts readily cleaved PARP into 85 kDa and 24 kDa fragments (FIG. 1B, lane 3) and SREBP-2 into 55 kDa and 70 kDa fragments (FIG. 1C, lane 3). The sizes of the cleaved products of PARP and SREBP-2 were the same as observed in cells undergoing apoptosis [Kaufmann et al. (1993) Cancer Res. 53, 3976–3985; Wang et al. (1996) supra]. It is likely that this cleavage was the result of the activation of CPP32, and related enzymes such as SCA2/Mch3, which are known to cleave PARP and SREBPs at these positions [Fernandes-Alnemi et al. (1995) Cancer Res. 55, 6045–6052; Pai et al. (1996) Proc. Natl. Acad. Sci. USA 93, 5437–5442]. HeLa cell S-100 extract in the presence of dATP induced DNA fragmentation when incubated with hamster liver nuclei (FIG. 1D, lane 3). Such fragmentation did not occur with HeLa S-100 in the presence or absence of ATP, confirming the requirement for dATP (FIG. 1D, lanes 1 and 2).

Figure 2B:
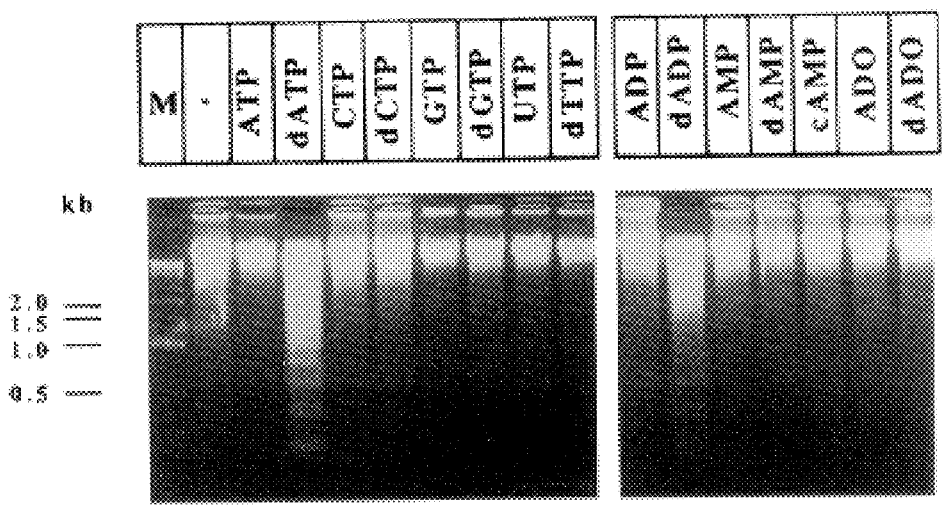

To test the nucleotide specificity for activation of CPP32 and DNA fragmentation, HeLa cell S-100 was incubated with in vitro translated, $^{35}$S-labeled CPP32 in the presence of 1 mM of various nucleotides (FIG. 2A). Cleavage occurred only in the presence of DATP or dADP (FIG. 2A). CTP, dCTP, GTP, dGTP, UTP, dTTP, ADP, AMP, dAMP, adenosine, deoxyadenosine and cAMP did not replace dATP. Identical nucleotide specificity was observed in the DNA fragmentation assay (FIG. 2B).

Figure 3:
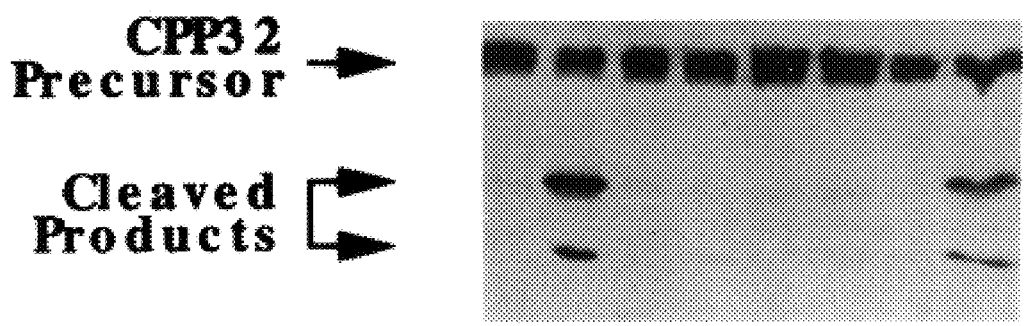
FIG. 3 illustrates fractionation and reconstitution of dATP-dependent activation of CPP32 by phosphocellulose chromatography. HeLa cell S-100 was subjected to phosphocellulose chromatography and the column flow through and bound material were collected as described in the Examples. Aliquots (10 µl) of HeLa S-100 (50 µg) (lanes 1 and 2), phosphocellulose flow through fraction (PC-FT) (lanes 3 and 4), phosphocellulose bound fraction (PC-B) (lanes 5 and 6), and the mixture of phosphocellulose flow through and bound material (lanes 7 and 8) were incubated with aliquots of 3 μl in vitro translated, $^{35}$S-labeled CPP32 at 30° C. for 1 hr in the absence (lanes 1,3,5,7) or presence (lanes 2,4,6,8) of 1 mM dATP. The samples were subjected to SDS-PAGE, transferred to a nitrocellulose filter, and the filter was exposed to film for 16 hours at room temperature.

To isolate the protein(s) required for the activation of CPP32, HeLa S-100 was loaded onto a phosphocellulose column, and the flow-through and bound fractions were collected. Neither fraction alone supported dATP-dependent activation of CPP32 (FIG. 3, lanes 3–6). When the flowthrough and bound fractions were mixed, CPP32-activating activity was restored (lanes 7–8). This experiment indicates that there are multiple factors, which can be separated by the phosphocellulose chromatography, contributing to dATP-dependent activation of CPP32. The factor(s) that flow through the phosphocellulose column are designated apoptotic protease activating factor-1 (Apaf-1) and the factor that bound to the column is designated apoptotic protease activating factor-2 (Apaf-2). It is understood that "Apaf-1" may represent more than one protein or it may represent a combination of protein(s) and other factors.

Figure 4A:
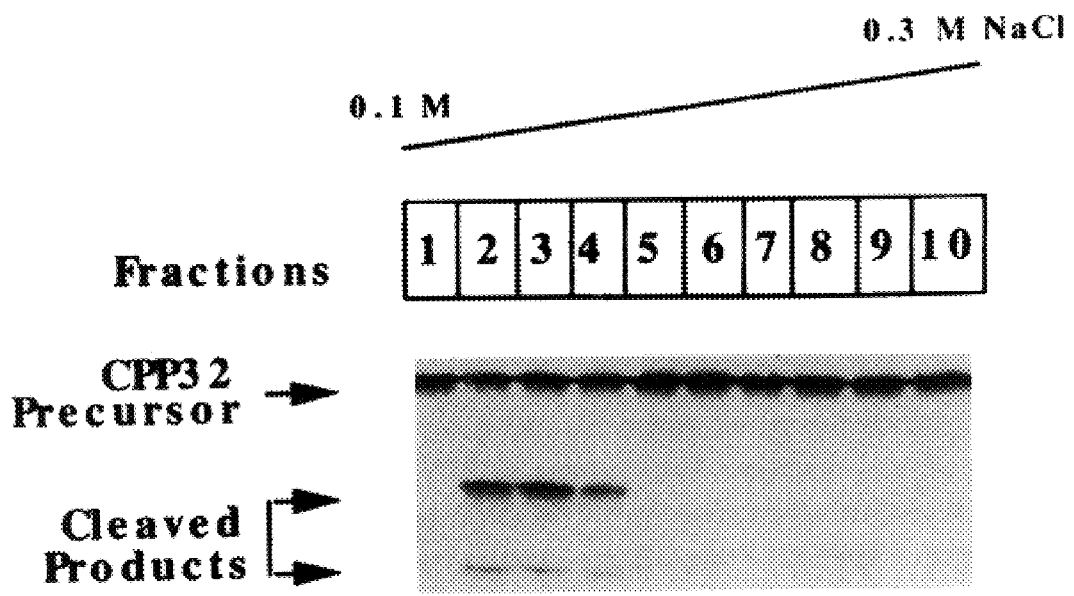
FIG. 4A shows the results of incubation of 1 μl aliquots of Mono S column fractions with aliquots of 10 μl phosphocellulose flow through fraction and 3 μl of in vitro translated, $^{35}$S-labeled CPP32 at 30° C. for 1 hr in the presence of 1 mM dATP in a final volume of 20 μl of buffer A. Samples were subjected to SDS-PAGE, transferred to a nitrocellulose filter, and the filter was exposed to film for 16 hours at room temperature.
Figure 4B:
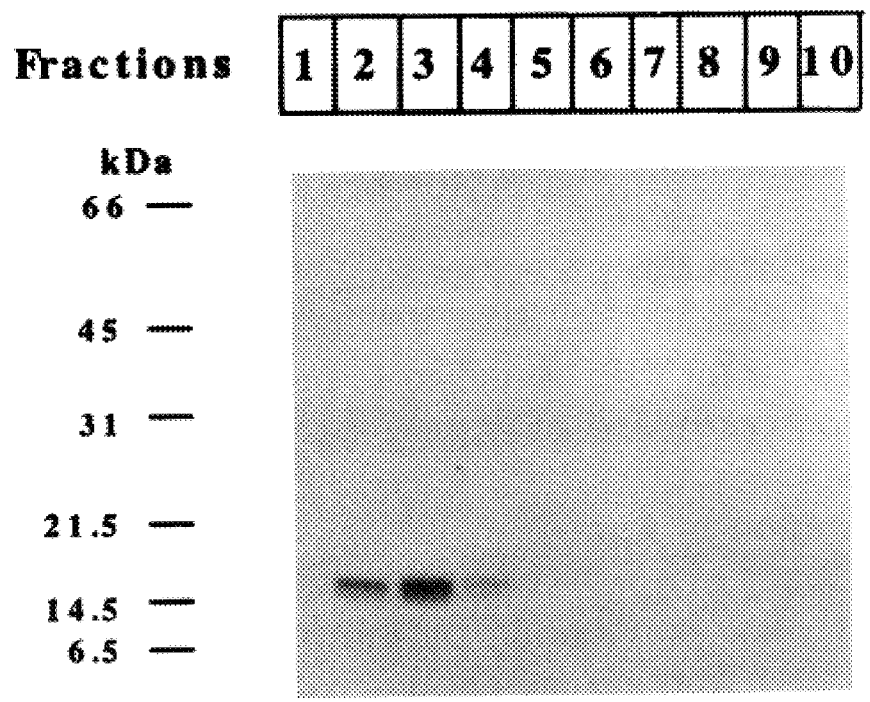
In FIG. 4B, aliquots (30 μl) of the Mono-S fractions were subjected to 15% SDS-PAGE and the proteins were visualized by silver staining.
Figure 5:
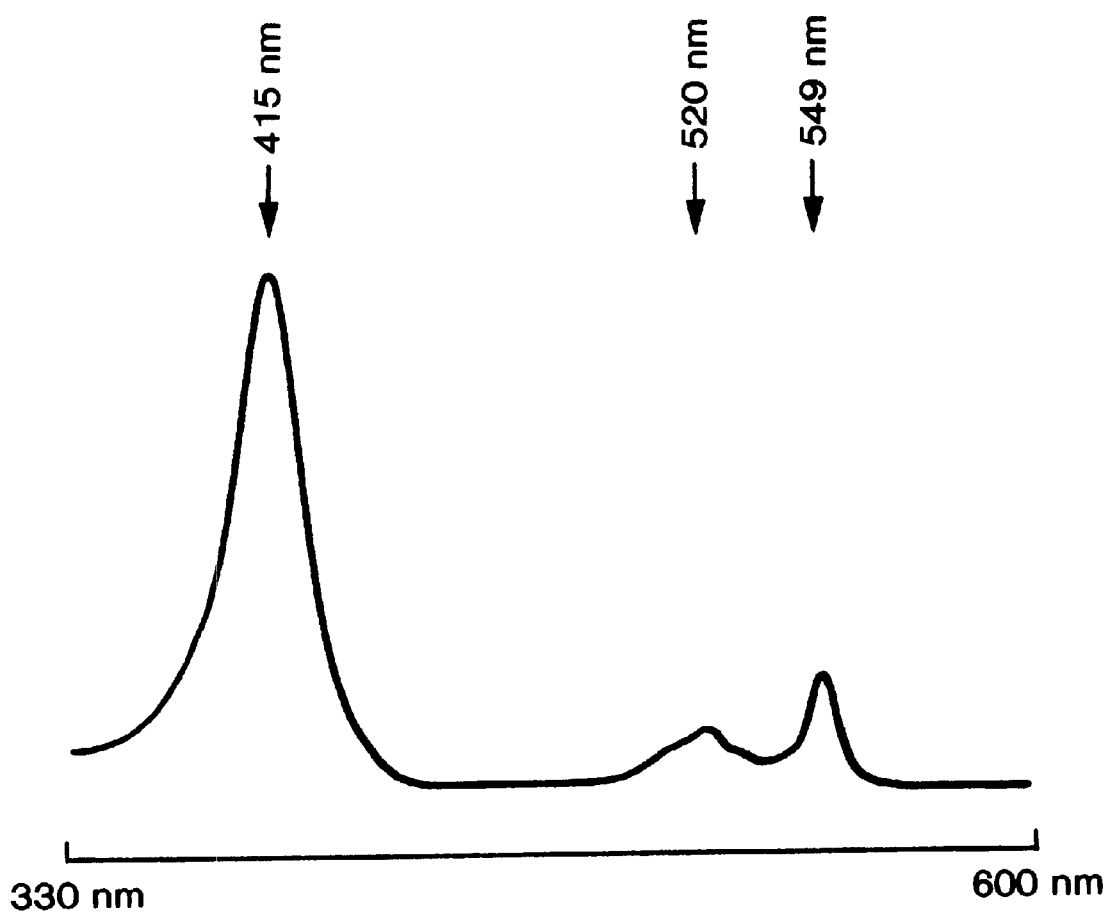
FIG. 5 provides the absorption spectrum of Apaf-2. An aliquot of 1 ml of Apaf-2 purified through the Mono S column was subjected to absorption spectrum scanning using a CARY 219 spectrophotometer. Absorption spectrum was recorded between 330 nm and 600 nm at a scanning speed of 1 mn/sec.

Apaf-2 activity was assayed by recombining with Apaf-1 after purification by the following steps. First, the Apaf-2 fraction was subjected to 50% ammonium sulfate precipitation. All of the activity remained in the supernatant while most of the protein precipitated (Table I). The supernatant was loaded onto a phenyl-sepharose (hydrophobic interaction) column and the activity was eluted with 1 M ammonium sulfate. The eluate was passed through a gel filtration column; active fractions were subjected to sequential Mono Q (anion exchange) and Mono S (cation exchange) chromatography. The Apaf-2 activity flowed through the Mono Q column, and the flow through was directly loaded onto the Mono S column. Bound Apaf-2 activity was then eluted with a 100–300 mM NaCl linear salt gradient. The fractions from the Mono S column were collected and assayed. As shown in FIG. 4A, the Apaf-2 activity eluted from the Mono S column at approximately 120 mM NaCl (fractions 2–4). The active fractions were analyzed by SDS-PAGE (FIG. 4B). A protein of apparent molecular mass of 15 kDa was co-eluted with the activity. No other proteins were detected by silver staining in the active Apaf-2 fractions.

Table I summarizes the results of a complete purification of Apaf-2 starting with the S-100 fraction from 20-liters of HeLa cells (348.5 mg protein). The Apaf-2 protein was purified more than 2000-fold with an overall recovery of 152% activity. The >100% recovery indicates the elimination of inhibitory activities during the purification.

Purified Apaf-2 had a noticeable pink color, and it showed absorbance peaks at 415, 520 and 549 nm, a spectrum shared by reduced cytochrome c [Margoliash and Walasek (1967) Meth. Enzymol. X, 339–348]. Identity of Apaf-2 with cytochrome c was confirmed by comparison of amino acid sequences generated from tryptic peptides isolated from the 15 kDa Apaf-2 with known cytochrome c amino acid sequence information. All those sequences show 100% identity with portions of the reported sequence of human cytochrome c (Table II).

Figure 6:
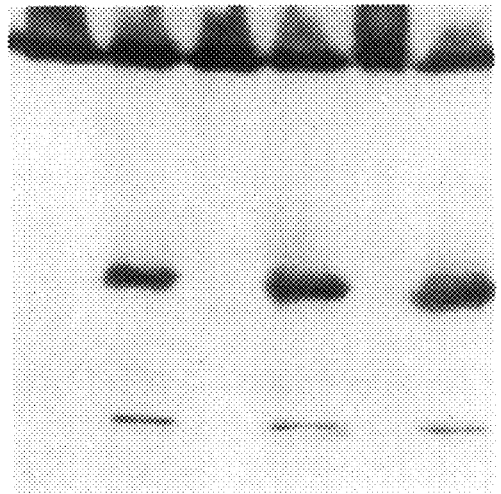
FIG. 6 demonstrates that cytochrome c proteins from bovine heart and rat liver have Apaf-2 activity. Aliquots of 0.2 μg of Apaf-2 purified through the Mono S column (lanes 1, 2), cytochrome c from bovine heart (lanes 3, 4), and rat liver (lanes 5, 6) were incubated with aliquots of 10 μl phosphocellulose flowthrough fraction and 3 μl in vitro translated, 35S-labeled CPP32 at 30° C. for 1 hr in a final volume of 20 μl buffer A in the absence (lanes 1,3,5) or presence of (lanes 2, 4, 6) 1 mM dATP. Samples were subjected to SDS-PAGE and transferred to a nitrocellulose filter which was then exposed to a film for 16 hr at room temperature.

To confirm that cytochrome c has Apaf-2 activity, purified bovine heart and rat liver cytochrome c (from a commercial source) were tested for Apaf-2 activity. As shown in FIG. 6, cytochrome c from both sources initiated dATP-dependent activation of CPP32 as efficiently as Apaf-2 (lanes 3–6).

Figure 7A:
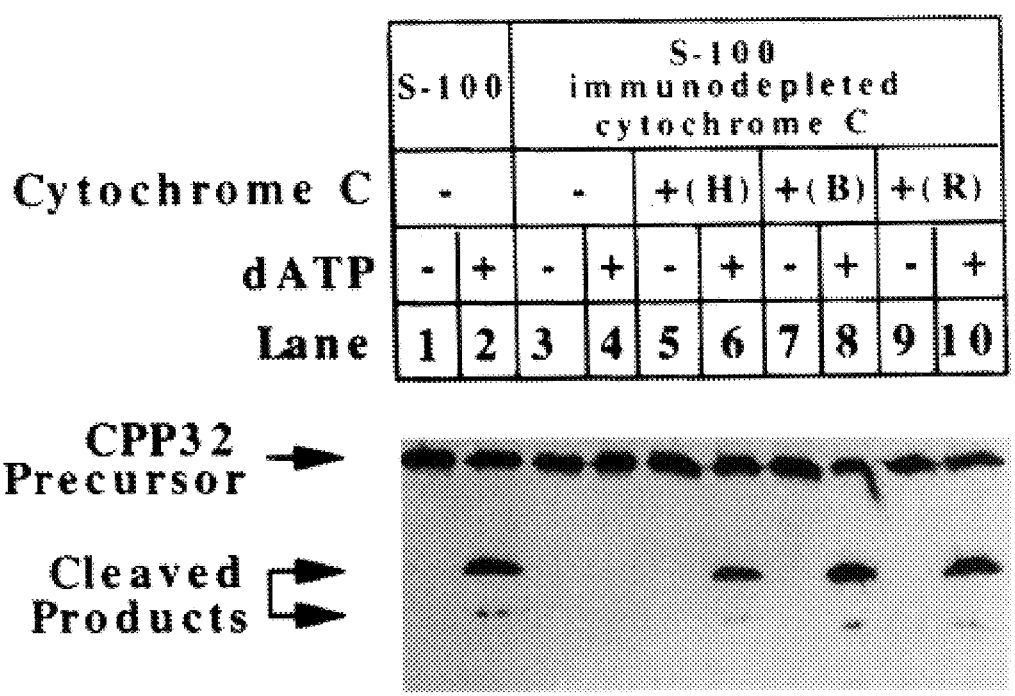
FIGS. 7A–7D demonstrate immunodepletion of cytochrome c from HeLa S-100 and reconstitution of dATP-dependent activation of CPP32, DNA fragmentation and nuclear morphological change using purified cytochrome c. Cytochrome c present in the HeLa cell S-100 was immunodepleted as described in the Example 10.
Figure 7B:
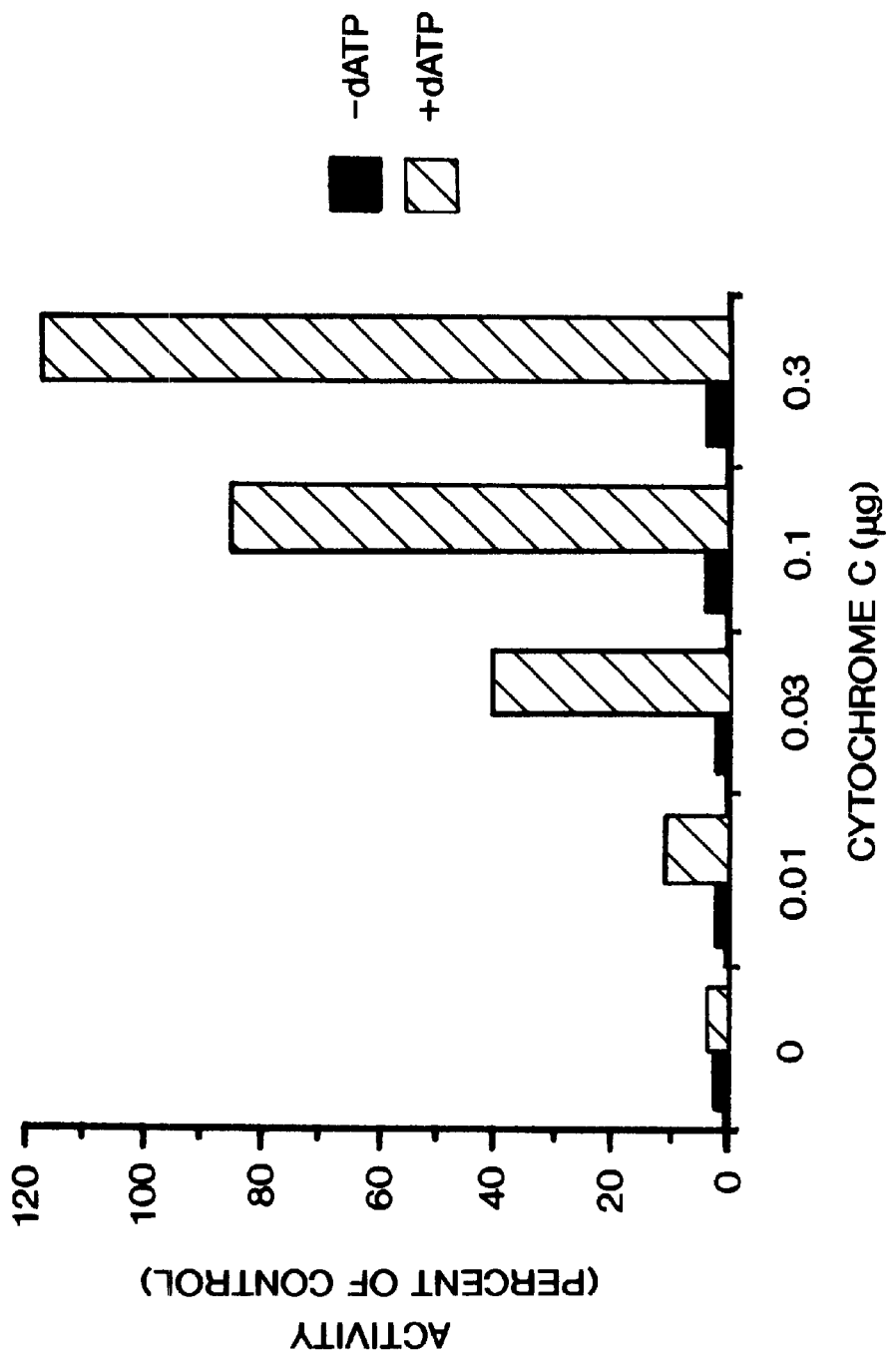
Figure 7C:
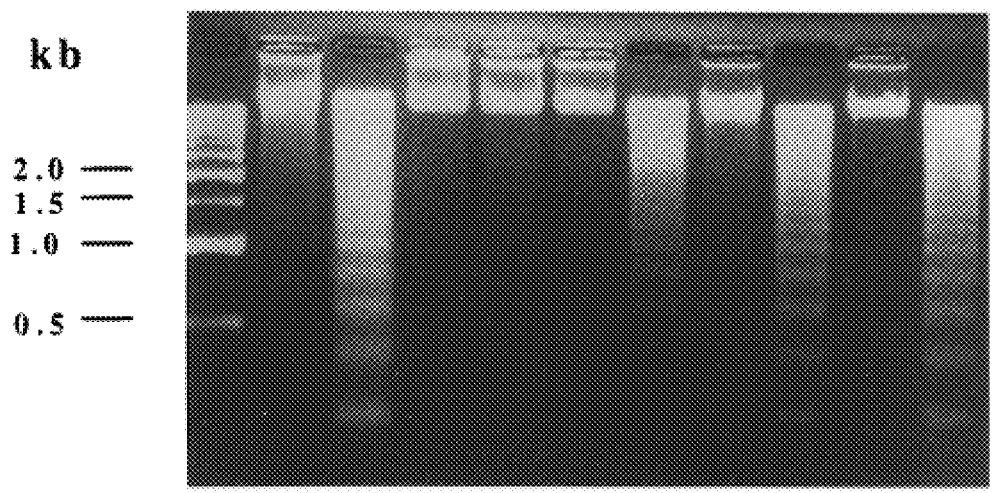
Figures 1, 7D:
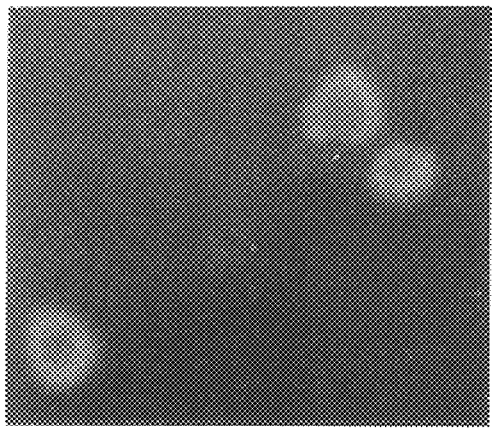
Figures 2, 7D:
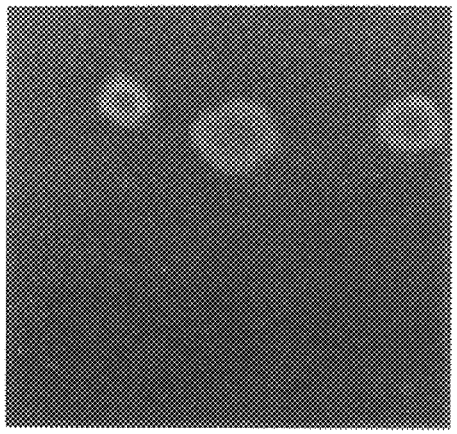
Figures 3, 7D:
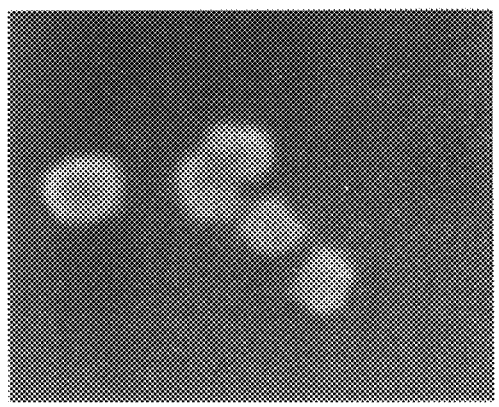
Figures 4, 7D:
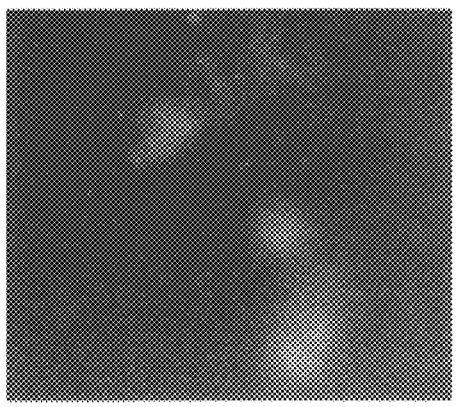
FIG. 4 shows the results of Mono S column purification of Apaf-2. The Apaf-2 activity that bound to the phosphocellulose column was purified through the Mono S column as described in Example 7.

To rule out the possibility that the Apaf-2 activity is due to a minor contaminating protein that co-purified with cytochrome c, an immunodepletion experiment was carried out using a monoclonal antibody against rat cytochrome c. This monoclonal antibody cross-reacts with purified Apaf-2. As shown in FIGS. 7A–7D, HeLa cell S-100 depleted of cytochrome c using the monoclonal anti-cytochrome c antibody lost the dATP-dependent activation of CPP32 and the ability to induce DNA fragmentation in the added nuclei (FIGS. 7A and 7C, lanes 3 and 4). Adding back either the purified Apaf-2 from HeLa cells or the commercial cytochrome c from bovine heart or rat liver to the immunodepleted extracts restored the dATP-dependent activation of CPP32 and DNA fragmentation (FIGS. 7A and 7C, lanes 5–10). The reconstitution of cytochrome c dependent-activation of CPP32 was evident with the addition of 0.01 μg (33 nM) of purified cytochrome c to the cytochrome c-depleted extracts (FIG. 7B). Addition of 0.3 μg of cytochrome c recovered more than 100% of control activity, indicating that the cytochrome c in the cytosol is not at saturation level (FIG. 7B). The DATP and cytochrome c-dependent activation of CPP32 and DNA fragmentation was accompanied by the morphological change in the co-incubated nuclei that is characteristic of apoptosis (FIG. 7D).

Figure 8:
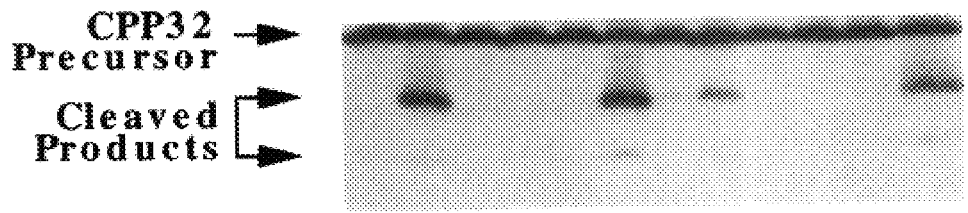
FIG. 8 illustrates dATP and cytochrome c-dependent activation of CPP32 in S-100 cytosol preparations (immunodepleted of cytochrome c) from human embryonic kidney 293 cells and human monoblastic U937 cells. CPP32 activation reactions were carried out as described in FIG. 7 except 25 μg of S-100 was used in each reaction. 1 mM of dATP was present in lanes 2, 4, 6, 8, 10, and 12. Lanes 1 and 2, S-100 fraction from 293 cells; Lanes 3–4, S-100 fraction from 293 cells immunodepleted of cytochrome c; lanes 5 and 6, S-100 fraction from 293 cells immunodepleted of cytochrome c supplemented with 0.2 μg of Apaf-2 purified through the Mono S column step; Lanes 7 and 8, S-100 fraction from U937 cells; Lanes 8–9, S-100 fraction from U937 cells immunodepleted of cytochrome c; lanes 11,12, S-100 fraction from U937 cells immunodepleted of cytochrome c supplemented with 0.2 μg of Apaf-2 purified through Mono S column step.

To investigate whether the dATP and cytochrome c-dependent activation of CPP32 is a general phenomenon, cytosols were prepared from human embryonic kidney 293 cells and human monoblastic leukemia U937 cells. As shown in FIG. 8, S-100 fractions from both cell types contained a dATP-dependent CPP32 activating activity (Lanes 1, 2 and 7, 8). Immunodepletion of cytochrome c from these cytosols resulted in the loss of CPP32 activating activity (lanes 3, 4 and 9, 10) and addition of purified cytochrome c restored the activity (lane 5, 6 and 11, 12).

Figure 9:
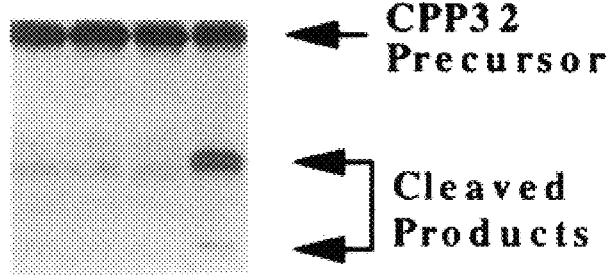
FIG. 9 demonstrates reconstitution of dATP-dependent activation of CPP32 with S-cytosol and purified Apaf-2. On day 0, Hela cells were set up at 5×10$^5$ cells per 100 mm dish in medium A as described hereinbelow. On day 2, cells were harvested, collected by centrifugation (1000 g, 10 min, 4° C.). After washed once with ice-cold PBS, the cell pellet was suspended in 5 volumes of ice-cold buffer A containing 250 mM sucrose. The cells were disrupted by douncing 3 times in a 5 ml Wheaton douncer with a pestle polished with sand paper. After microcentrifugation for 5 min at 4° C., the supernatants were further centrifuged at 10$^5$×g for 30 min in a table top ultracentrifuge (Beckman Instruments, Fullerton, Calif.). The resulting supernatants were designated as S-cytosol. Aliquots of S-cytosol (50 μg) alone (lanes 1 and 2), or supplemented with 0.2 μg Apaf-2 purified through the Mono S column (lanes 3 and 4), were incubated with aliquots of 3 μl in vitro translated, $^{35}$S-labeled CPP32 in the absence (lanes 1, 3) or presence (lanes 2, 4) of 1 mM dATP at 30° C. for 1 hr in a final reaction volume of 20 μl of buffer A. Samples were subjected to SDS-PAGE and transferred to a nitrocellulose filter which were then exposed to film for 16 hr at room temperature.
Figure 10A:
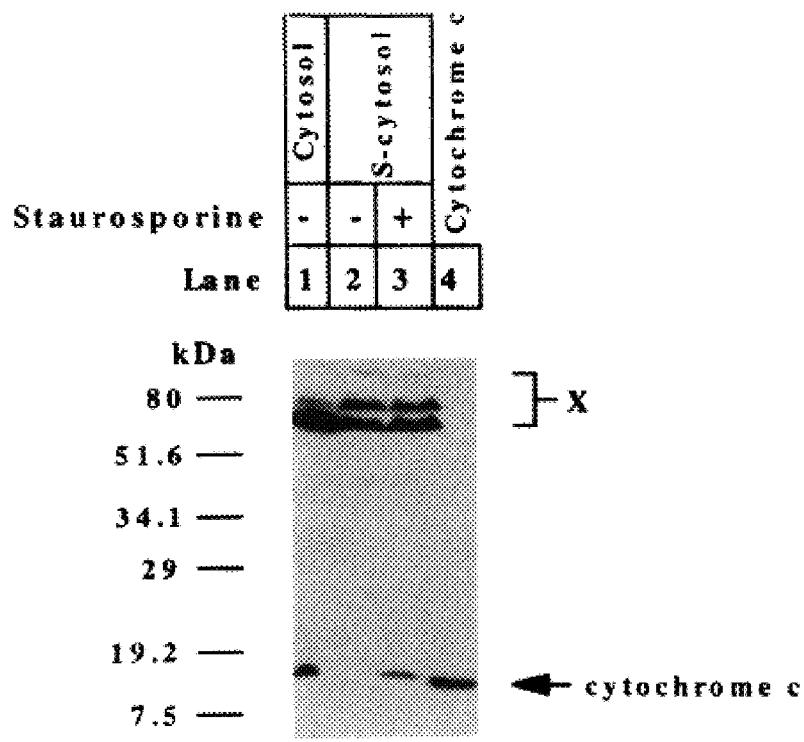
FIGS. 10A–10B shows increased release of cytochrome c to the cytosol upon apoptotic stimulation. HeLa cells were treated as described in FIG. 9. On day 2, staurosporine at a final concentration of 1 μM was added to the medium as indicated. After incubation at 37° C. for 6 hr, the cells were harvested and S-cytosols were prepared as described in FIG. 9.

Human cytochrome c is encoded by a single copy nuclear gene [Evans and Scarpulla (1988) Proc. Natl. Acad. Sci. USA 85, 9625–9629] which is translated on cytoplasmic ribosomes as apocytochrome c. The heme group of cytochrome c is attached to apocytochrome c upon its translocation into mitochondria; holocytochrome c is a soluble protein located in the intermembrane space of mitochondria [Gonzales and Neupert (1990) J. Bioenergetics & Biomembranes 22, 753–768]. The presence of cytochrome c in the cytosolic fraction can therefore be the result of ruptured outer mitochondrial membrane by hypotonic shock during its preparation. To test this hypothesis, cytosol from HeLa cells was prepared in the presence of 250 mM sucrose to protect mitochondrial integrity. The cells were broken gently by douncing in a sand paper polished piston [Hayakawa et al. (1993) Mol. Cell. Biochem. 119, 95–103]. Cytosol prepared this way (designated S-cytosol) contained little cytochrome c as compared to the cytosol used in the previous experiments (FIG. 10A, lanes 1 and 2). As shown in FIG. 9, S-cytosol was incapable of initiating the dATP-dependent activation of CPP32 (lanes 1 and 2) unless purified cytochrome c was added (lanes 3 and 4).

Figure 10B:
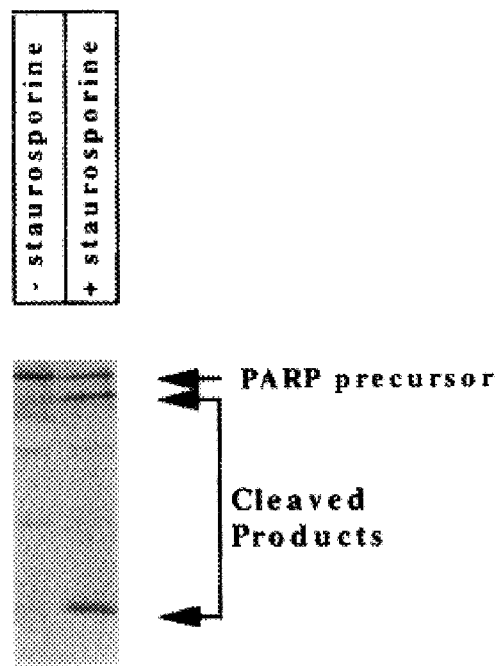

The requirement for cytochrome c in the apoptotic program in vitro indicates there is increased release of cytochrome c to the cytosol in cells undergoing apoptosis. HeLa cells were treated with staurosporine. Staurosporine is a broad-spectrum inhibitor of protein kinases, and it has been found to be a potent apoptosis inducer in a variety of cell types [Rueggs and Burgess (1989) Trends Pharmacol. Sci. 10, 218–220; Jacobson et al. (1993) Nature 361, 365–36; Wang et al. (1996) supra]. Cytosol was prepared from staurosporine-treated cells using sucrose containing buffer, and the cells were dounced by the sand paper polished piston. As shown in FIG. 10B, staurosporine treatment of HeLa cells resulted in activation of the endogenous CPP32 as detected by the cleavage of PARP. S-cytosol from staurosporine-treated HeLa cells contained markedly elevated cytochrome c as compared to that from non-treated cells (FIG. 10A, lanes 2 and 3). The same phenomenon was also observed in human monoblastic U937 cells. Arabinosylcytosine, etoposide and mitoxantrone HCl also act to initiate apoptosis.

The present invention provides an in vitro system that faithfully duplicates the two best characterized biochemical markers of apoptosis, i.e. DNA fragmentation into nucleosomal fragments and the activation of the ICE-related apoptotic protease CPP32. This in vitro system allowed us to fractionate and begin to isolate the required components. One required protein factor was purified to homogeneity and identified as the human cytochrome c.

The present dATP- and cytochrome c-dependent in vitro apoptosis system represents a general apoptotic program. Identical results were obtained from cytosols of HeLa cells, human embryonic kidney 293 cells, and human monoblastic U937 cells.

There have been several previous reports of cell-free apoptosis systems based on extracts from hormone-reated Xenopus eggs [Newmeyer et al. (1994) supra], double synchronized mitotic chicken hepatoma cells (Lazebnik et al. (1993) supra], or extracts from Fas, UV irradiated and ceramide treated cells [Eeari et al. (1995) supra; Martin et al. (1995) supra]. Our system differs from the previously reported systems in that it uses extracts from normally growing cells which have not been induced to undergo apoptosis. This allows apoptosis to be initiated in vitro. Because it uses only soluble components, the system is amenable to fractionation and reconstitution.

In vitro apoptosis in our system was initiated by the addition of dATP. Although the finding that dATP plays a critical role for initiation of apoptosis in vitro was empirical, dATP has long been implicated in cell death. The best known case is the inherited deficiency of adenosine deaminase (ADA), which results in severe combined immunodeficiency (SCID). In ADA patients, there is an abnormal accumulation of dATP up to mM level in their lymphocytes and death of $CD8^{low}$ transitional and CD4–CD8 double-positive thymocytes by an apoptosis mechanism [Cohen et al. (1978) Proc. Natl. Acad. Sci. USA 75, 472–476; Goday, A. et al. (1985) Biochem. Pharm. 34, 3561–3569; Benveniste and Cohen (1995) Proc. Natl. Acad. Sci. USA 92, 8373–8377]. It has also been reported that deoxyadenosine treatment of cultured chick embryonic sympathetic neurons results in the accumulation of dATP and death through apoptosis [Wakade et al. (1995) *J. Biol. Chem.* 270, 17986–17992]. Neuronal cell death was prevented by an nucleotide kinase inhibitor, suggesting that DATP accumulation was the cause of cell death [Wakade et al. (1995) supra]. Our finding that dATP can initiate the activation of CPP32 and DNA fragmentation provides a mechanistic explanation for the dATP mediated cell toxicity. dADP can substitute for dATP. In cells treated with an ADA inhibitor, dADP also accumulates, although to a lesser extent than dATP [Goday et al. (1985) supra].

The fractionation of the factors necessary for dATP-dependent activation of CPP32 resulted in the identification of soluble cytochrome c as one of the necessary components for apoptosis in vitro. It is unlikely that cytochrome c mimics the function of another protein, because cytochrome c is the only protein with Apaf-2 activity purified from the S-100 fraction. The requirement for cytochrome c was confirmed by the depletion and reconstitution experiments.

Cytochrome c is an essential component of the mitochondrial respiratory chain. It is a soluble protein which is localized in the intermembrane space and is loosely attached to the surface of the inner mitochondrial membrane [Gonzales and Neupert (1990) supra]. Cytochrome c is translated by cytoplasmic ribosomes and follows a unique pathway into mitochondria which does not require the signal sequence, electro-chemical potential, and general protein translocation machinery [Mayer et al. (1995) *J. Biol. Chem.* 270, 12390–12397].

Mitochondria have been implicated in apoptosis since the discovery that the bcl-2 family of proteins are located in the outer mitochondrial membrane [Monaghan et al. (1992) supra; Krajewski et al. (1993) supra; de Jong et al. (1994) supra]. In vitro apoptosis in Xenopus egg extracts requires a dense organelle fraction enriched in mitochondria [Newmeyer et al. (1994) supra]. The present inventors have shown that purified mitochondria from hamster heart can supplement cytosol immunodepleted of cytochrome c, or cytosol prepared in the presence of sucrose to support CPP32 activating reaction. However, a potential argument against the involvement of mitochondria in apoptosis comes from a report that apoptosis and bcl-2 protection of apoptosis are normal in cells lacking mitochondria DNA [Jacobson et al. (1993) supra]. None of the known mitochondrial functions, such as ATP production, electron transfer, oxidative phosphorylation, generation of reactive oxygen species and $Ca^{2+}$ uptake, appear to account for its involvement in apoptosis [Jacobson et al. (1993) supra; Hockenbery et al. (1993) *Cell* 75, 241–251; Newmeyer et al. (1994) supra]. That cytochrome c is a necessary component of cellular apoptotic program indicates that mitochondria are involved in apoptosis by releasing cytochrome c. Because cytochrome c is encoded by a nuclear gene and translocation of apocytochrome c into mitochondria does not require membrane potential and general protein translocation machinery [Evans and Scarpulla (1988) supra; Mayer et al. (1995) supra], it can be totally functional in apoptosis in cells lacking mitochondrial DNA. Consistent with this model, the cells undergoing apoptosis induced by staurosporine showed increased cytosolic cytochrome c. Release of cytochrome c into the cytosol provides a target for regulation of apoptosis, possibly by the bcl-2 family of proteins.

The biochemical mechanism of cytochrome c function in the activation of CPP32 remains to be determined. The purification and characterization of Apaf-1, which is at least one other component required for the CPP32 activation reaction, will provide further understanding of the early events in apoptosis.

Monoclonal or polyclonal antibodies, preferably monoclonal, specifically reacting with a target protein can be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York.

Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory Press, Plainview, N.Y.; Maniatis et al. (1982) *Molecular Cloning*, Cold Spring Harbor Laboratory Press, Plainview, N.Y.; Wu (ed.) (1993) *Meth. Enzymol.* 218, Part I; Wu (ed.) (1979) *Meth Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology;* Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; and Setlow and Hollaender (1979) *Genetic Engineering: Principles and Methods*, Vols. 1–4, Plenum Press, New York. Abbreviations and nomenclature, where employed, are deemed standard in the field and commonly used in professional journals such as those cited herein. All references cited herein are incorporated by reference in their entirety.

EXAMPLES

Example 1

General Methods and Materials

Nucleotide triphosphates were purchased from Pharmacia (Piscataway, N.J.). ADP, dADP, AMP, dAMP, adenosine and deoxyadenosine were from ICN Biomedicals, Inc. (Costa Mesa, Calif.). Pepstatin A, leupeptin, N-acetyl-leucyl-leucyl-norleucine (ALLN) were obtained from Boehringer Mannheim Corporation (Indianapolis, Ind.). Phenylmethylsulfonyl fluoride (PMSF), Imidazole, cAMP, aprotinin, bovine heart cytochrome c and rat liver cytochrome c were purchased from Sigma Chemical Co. (St. Louis, Mo.). $^{35}$S-methionine was purchased from Amersham Corporation (Arlington Heights, Ill.). Molecular weight standards for SDS-PAGE and gel-filtration chromatography were obtained from Bio-Rad Laboratories (Hercules, Calif.).

cDNA clones of human SREBP-2 and hamster CPP32 were described in Wang et al. (1995) and protein concentration was determined by the Bradford method [Bradford, M. M. (1976) *Anal. Biochem.* 72, 248–254]. Silver staining was carried out using a Silver Stain Plus kit from Bio-Rad Laboratories (Hercules, Calif.). Plasmids were purified using a Megaprep kit (Qiagen, Chatsworth, Calif.).

Example 2

Preparation of S-100 Fractions from HeLa Cells, 293 Cells and U937 Cells

Human HeLa S3 cells were grown as described [Wang et al. (1993) *J. Biol. Chem.* 268, 14497–14504]. The cells ($5\times10^5$/ml) were harvested by centrifugation at 1,800×g for 10 min at 4° C. After washed once with ice-cold phosphate buffered saline (PBS), the cell pellet was suspended in 5 volumes of ice-cold buffer A [20 mM Hepes-KOH, pH 7.5, 10 mM KCl, 1.5 mM $MgCl_2$, 1 mM sodium EDTA, 1 mM sodium EGTA, 1 mM dithiothreitol (DTT) and 0.1 mM PMSF] supplemented with protease inhibitors (5 µ/ml pepstatin A, 10 µg/ml leupeptin, 2 µml aprotinin, and 25 µg/ml ALLN). After holding on ice for 15 min, the cells were disrupted by douncing 15 times in a 100 ml Kontes douncer with the B pestle (Kontes Glass Co., Vineland, N.J.). The nuclei were centrifuged at 1000×g for 10 min at 4° C. The supernatant was further centrifuged at $10^5$×g for 1 hr in a Beckman SW 28 rotor. The resulting supernatant (S-100 fraction) was stored at −80° C. and used for the in vitro apoptosis assay and the starting material for the purification of Apaf-2.

293 cells were set up at 5×$10^5$ cells per 100 mm dish in medium A [Dulbecco's modified Eagle's medium (DMEM) supplemented with 10% (v/v) heat-inactivated fetal calf serum, 100 U/ml penicillin and 100 µg/ml streptomycin sulfate]. After incubation for 48 hr at 37° C. in a 5% $CO_2$ incubator, the cells were harvested, collected by centrifugation (1000 g, 10 min, 4° C.). U937 cells were set up at 5×$10^5$ cell/ml in medium B [RPMI 1640 medium supplemented with 10% fetal calf serum, 100 U/mil penicillin and 100 µg/ml streptomycin sulfate]. After incubation for 48 hr in a 5% $CO_2$ incubator, the cells were collected by centrifugation (1000 g, 10 min, 4° C.). The cell pellets of 239 cell and U937 cell were washed once with ice-cold PBS and resuspended in 5 volumes of ice-cold buffer A supplemented with protease inhibitors. After holding on ice for 15 min, the cells were broken by passing 15 times through a G22 needle. After centrifugation in a microcentrifuge for 5 min at 4° C., the supernatants were further centrifuged at $10^5$×g for 30 min in a table top ultracentrifuge (Beckman Instruments, Fullerton, Calif.). The resulting supernatants were used for the in vitro apoptosis assay.

Example 3

In vitro Translation of CPP32, SREBP, and PARP

A PCR fragment encoding amino acids 29–277 of hamster CPP32 [Wang et al. (1996) supra] was cloned into NdeI and BamHI sites of pET 15b vector (Novagen, Madison, Wis.). The resulting fusion protein of six histidines with hamster CPP32 (amino acids 29–277) was translated in a TNT T7 transcription/translation kit (Promega, Madison, Wis.) in the presence of $^{35}$S-methionine according to the manufacturer's instructions. The translated protein was passed through a 1 ml nickel affirmity column (Qiagen, Chatsworth, Calif.) equilibrated with buffer A. After washing the column with 10 ml of buffer A, the translated CPP32 was eluted with buffer A containing 250 mM imidazole. Human SREBP-2 was translated in a TNT SP6 transcription/translation kit as described [Wang et al. (1995) [Hua et al. (1993) Proc. Natl. Acad. Sci. USA 90, 11603–11607]. Full length human PARP cDNA [Chemey et al. (1987) Proc. Natl. Acad. Sci. USA 84, 8370–8374] was cloned into SmaI and EcoRI sites of pBK-CMV vector (Stratagene, La Jolla, Calif.) and translated in a TNT T7 transcription/translation kit [Promega, Madison, Wis.]. The translated SREBP-2 and PARP (200 µl each) were purified by passing each translation mixture through a 10-ml Sephadex G-25 gel-filtration column equilibrated with buffer A. The translated proteins contained within the exclusion volume of the column were collected.

Example 4

Western Blot Analysis

A monoclonal antibody against human CPP32 was purchased from Transduction Laboratories and a monoclonal antibody against cytochrome c (7H8.2C12) was obtained as described previously [Jemmerson and Johnson (1991) Proc. Natl. Acad. Sci. USA 88, 4428–4432]. Monoclonal antibody specific for cytochrome c is available from Pharmingen. Immunoblot analysis was performed with horseradish peroxidase-conjugated anti-mouse immunoglobulin G using the Enhanced Chemiluminescence (ECL) Western Blotting Detection reagents (Amersham Corporation, Arlington Heights, Ill.).

Example 5

Assay for dATP-dependent Activation of CPP32 Protease

CPP32 was translated and purified as described above. Aliquot of 3 µl of the in vitro translated CPP32 was incubated with the indicated protein fraction, nucleotides, and 1 mM additional $MgCl_2$ at 30° C. for 1 hour in a final volume of 20 µl of buffer A. At the end of the incubation, 7 µl of 4×SDS sample buffer was added to each reaction. After boiling for 3 min, each sample was subjected to a 15% SDS-polyacrylamide gel electrophoresis (SDS-PAGE). The gel was transferred to a nitrocellulose filter which was subsequently exposed to a Kodak X-OMAT AR X-ray film (Eastman Kodak, Rochester, N.Y.) for 16 hr at room temperature.

Example 6

Purification of Apaf-2 from HeLa S-100

All purification steps were carried out at 4° C. All the chromatography steps except the phosphocellulose column were carried out using an automatic fast protein liquid chromatography (FPLC) station (Pharmacia, Piscataway, N.J.).

85 ml of HeLa S-100 was applied to a phosphocellulose column (40 ml bed volume) equilibrated with Buffer A. The column was washed with 3 column volumes of buffer A and eluted with 2 column volumes of buffer A containing 0.5 M NaCl. Ammonium sulfate (50%) was added directly to the phosphocellulose 0.5 M eluate. After rotating at 4° C. for 1 h, the mixture was centrifuged at 15,000 rpm for 15 min in a JA 20 rotor (Beckman Instruments, Fullerton, Calif.). The supernatant was directly applied to a 10 ml phenyl-agarose column [phenyl-sepharose, Pharmacia, Piscataway, N.J.] equilibrated with buffer A containing 50% ammonium sulfate. The column was washed with two bed volumes of buffer A containing 50% ammonium sulfate and eluted with buffer A containing 1 M ammonium sulfate. The eluate was loaded onto a Superdex-200 gel filtration column (Pharmacia, Piscataway, N.J.) (300 ml) equilibrated with buffer A and eluted with the same buffer. Fractions of 10 ml were collected and assayed for Apaf-2 activity. The active fractions from the gel-filtration column were pooled and loaded onto an anion exchange Mono Q 5/5 column and a cation exchange Mono S 5/5 column connected together. The columns were pre-equilibrated with Buffer A. After loading, the columns were disconnected and the Mono S column was washed with 5 ml of buffer A containing 0.1 M NaCl and the Apaf-2 activity was eluted from the column with a 20 ml 0.1–0.3 M linear NaCl gradient. Fractions of 1 ml were collected.

Example 7

Preparation of Hamster Liver Nuclei

Livers from 4 male Golden Syrian hamsters (Sasco) were rinsed with ice-cold phosphate-buffered saline (PBS) and homogenized in 0.25 g/ml of buffer B (10 mM Hepes-KOH, pH 7.6, 2.4 M sucrose, 15 mM KCl, 2 mM sodium EDTA, 0.15 mM spermine, 0.15 mM spermidine, 0.5 mM DTT, 0.5 mM PMSF) by three strokes of a motor-driven homogenizer. The homogenates were centrifuged through a 10-ml cushion of buffer B at 25,000 rpm for 1 h in a SW 28 rotor at 4° C. The nuclei pellet was resuspended in buffer C (10 mM PIPES, pH 7.4, 80 mM KCl, 20 mM NaCl, 5 mM sodium EGTA, 250 mM sucrose, and 1 mM DTT) at $8.5 \times 10^7$ nuclei/ml and stored at −80° C. in multiple aliquots.

Example 8

DNA Fragmentation Assay

Aliquots of 50 μl HeLa cell S-100 and 6μl hamster liver nuclei were incubated at 37° C. for 2 h with 1 mM additional $MgCl_2$ in the absence or presence of 1 mM indicated nucleotide. After incubation, an aliquot of 500 μl buffer D (100 mM Tris-HCl, pH 8.5, 5 mM EDTA, 0.2 M NaCl, 0.2% w/v SDS, and 0.2 mg/ml proteinase K) was added to each reaction and incubated at 37° C. overnight. NaCl was then added to a final concentration of 1.5 M, and the nuclear debris was spun down for 15 min in a microcentrifuge at room temperature. The DNA in the supernatant was precipitated with an equal volume of 100% (v/v) ethanol. The DNA precipitate was washed once with 70% ethanol and resuspended in 40 μl of buffer E containing 10 mM Tris-HCl, pH 7.5, 1 mM sodium EDTA, and 200 μg/ml DNAse-free RNase A (Worthington Biochemical Corporation, Freehold, N.J.). After incubation at 37° C. for 2 hr, the DNA was loaded onto a 2% agarose gel and electrophoresis was conducted at 50 V for 2 hr in 0.5×TBE buffer (1×TBE buffer contains 90 mM Tris-borate/2 mM EDTA). The gel was stained with 2 μg/ml ethidium bromide for 15 min, destained with water for 1 hr, and the DNA was visualized using UV light.

Example 9

Immunodepletion of Cytochrome c from HeLa S-100

An anti-cytochrome c monoclonal antibody (6H2. B4) which recognizes the native form of cytochrome c was described previously [Jemmerson et al. (1991) *Eur. J. Immunol.* 21, 143–151]. An aliquot of 100 μl (0.7 mg/ml of IgG 2A) of this antibody was incubated with a 1:1 mixture of 50 μl protein A and protein G agarose beads resuspended in 200 μl of PBS (Santa Cruz) at 4° C. for 3 hr. The beads were collected by centrifugation for 15 min in a microcentrifuge at 4° C. After removal of the supernatant, the beads were washed once with 1 ml of buffer A and incubated with 1.5 ml S-100 fractions for 5 hr in a rotator at 4° C. The beads were subsequently pelleted by centrifugation for 15 min in a microcentrifuge at 4° C. The supernatant was used as S-100 immunodepleted of cytochrome c.

The foregoing examples and disclosure are provided for illustrative purposes, and they are not intended to limit the scope of the invention as provided herein. Any variations in the exemplified compositions and methods which occur to the skilled artisan are intended to fall within the scope of the present invention.

TABLE I

Purification of Apaf-2 from HeLa cells
S-100 was prepared from 20-liters of HeLa cells in spinner culture as described in the Examples. An aliquot of each fraction was dialyzed against buffer A and the Apaf-2 activity was assayed by recombining with $^{35}$S-labeled CPP32 at four concentrations of protein. The results were quantified by phosphorimaging.

| Step | Fraction | Protein mg | Specific Activity units/mg | Total Activity unit | Purification-fold | Recovery % |
|---|---|---|---|---|---|---|
| 1 | S-100 | 348.5 | | | | |
| 2 | Phosphocellulose | 104 | 126.6 | 13166 | 1 | 100 |
| 3 | 50% Ammonium-Sulfate Precipitation | 23.8 | 833.3 | 19824 | 6.6 | 150 |
| 4 | Phenyl-Sepharose | 0.473 | 42145 | 19934 | 333 | 151 |
| 5 | Superdex-200 | 0.460 | 43367 | 19950 | 343 | 152 |
| 6 | Mono Q/Mono-S | 0.076 | 263150 | 20000 | 2079 | 152 |

[a]Protein concentrations of various fractions were determined by the Bradford method.
[b]One unit of activity is defined as the cleavage of 1% of the input substrate in 60 min.

TABLE II

Sequences of tryptic peptides from the 15-kDa Apaf-2: comparison with human cytochrome c Sequences were obtained from Edman degradation performed on the HPLC-purified tryptic (Lys-C) peptides generated from the SDS-PAGE purified 15 kDa Apaf-2. The sequence of human cytochrome c was reported by Evans and Scarpulla, 1988, supra. The * denotes a residue in Apaf-2 that could not be assigned based on peptide sequence analysis. Numbers in parentheses denote the amino acid position in the cDNA sequence of human cytochrome c.

| Tryptic peptide | |
|---|---|
| 1. EERADLIAY (89–96) | (SEQ ID NO:1) |
| 2. TGPNLHGLFGR (28–38) | (SEQ ID NO:2) |
| 3. TGQAPGYSYTAANK (40–53) | (SEQ ID NO:3) |
| 4. YIPGTK (74–79) | (SEQ ID NO:4) |
| 5. *II*GEDTLMEYL (56–68) | (SEQ ID NO:5) |
| 6. IFIMK (9–13) | (SEQ ID NO:6) |
| 7. TGPNL (28–32) | (SEQ ID NO:7) |

We claim:

1. An in vitro method for assaying compositions for activation or inhibition of the initiation of apoptosis, said method comprising the steps of:
   (a) providing an S-100 cell extract supernatant, wherein said extract is prepared from disrupted eukaryotic cells and contains little or no cytochrome C, said cells having not been induced to undergo apoptosis;
   (b) contacting a candidate composition with the supernatant of step (a) in the presence of dATP or dADP and cytochrome C; and
   (c) detecting CPP32 protease activity or nuclease activity and comparing these activities to a control supernatant which was not contacted with the candidate composition, thereby identifying a candidate composition as an activator or inhibitor of apoptosis when the protease or nuclease activity is greater or less in the presence than in the absence of the candidate composition.

2. The method of claim 1 wherein said cells are mammalian cells.

3. The method of claim 2 wherein said cells are tumor cells.

4. The method of claim 3 wherein said cells express Bcl-2.

5. The method of claim 3 wherein said cells are HeLa cells.

6. The method of claim 3 wherein the step of detecting CPP32 protease activity comprises the addition of a detectable CPP32 substrate and detecting cleavage of said substrate.

7. The method of claim 2 wherein the detectable CPP32 substrate is a radioactive CPP32 substrate.

8. The method of claim 2 wherein the step of detecting CPP32 protease activity comprises the detectable CPP32 substrate is a detectable poly(adenosine diphosphate-ribose) polymerase (PARP) or a detectable sterol regulatory binding protein (SREBP).

9. The method of claim 8 wherein said SREBP is SREBP-2.

10. The method of claim 8 wherein said SREBP or PARP is radiolabeled.

11. The method of claim 8 wherein CPP32 protease activity is detected by sodium dodecyl sulfate-polyacrylamide gel electrophoresis.

12. The method of claim 2 wherein the step of detecting nuclease activity comprises the addition of nuclei containing genomic DNA and subsequently determining size distributions of the DNA as compared with the control supernatant which was not contacted with the test composition.

13. An in vitro method for assaying compositions for inhibition of the initiation of apoptosis, said method comprising the steps of:
   (a) providing an S-100 cell extract supernatant, wherein said extract is prepared from disrupted eukaryotic cells and contains little or no cytochrome C, said cells having not been induced to undergo apoptosis;
   (b) contacting a candidate composition with the supernatant of step (a) in the presence of dATP or dADP and cytochrome C; and
   (c) detecting CPP32 protease activity or nuclease activity and comparing these activities to a control supernatant which was not contacted with the candidate composition, thereby identifying a candidate composition as an inhibitor of apoptosis when the protease or nuclease activity is less in the presence than in the absence of the candidate composition.

14. The method of claim 13 wherein said eukaryotic cells are mammalian cells.

15. The method of claim 14 wherein the mammalian cells are HeLa cells.

16. The method of claim 14 wherein CPP32 protease activity is determined by introducing detectable polyadenosine diphosphate-ribose phosphate polymerase (PARP) or one or more detectable sterol regulatory binding proteins (SREBP) in step (b) and detecting an increase in fragments of the PARP or SREBP in the supernatant to which the candidate compound is added as compared to the control supernatant to which the candidate compound has not been added.

17. The method of claim 16 wherein said SREBP is SREBP-2.

18. The method of claim 16 wherein said detectable SREBP or said detectable PARP is radiolabeled.

19. The method of claim 16 wherein fragments of SREBP or PARP are determined by sodium dodecyl sulfate-polyacrylamide gel electrophoresis.

20. The method of claim 13 wherein said nuclease activity is measured by DNA fragmentation by introducing intact mammalian cell nuclei containing genomic DNA and determining size distributions of the DNA of the extracts with the candidate composition as compared with the control extract.

21. The method of claim 13 wherein the eukaryotic cells from which the extract supernatant is prepared are tumor cells.

22. The method of claim 21 wherein the tumor cells comprise a Bcl-2 protein.

* * * * *

SEQUENCE LISTING

```
(1) GENERAL INFORMATION:

(iii) NUMBER OF SEQUENCES: 7

(2) INFORMATION FOR SEQ ID NO:1:

(i) SEQUENCE CHARACTERISTICS:
         (A) LENGTH: 9 amino acids
         (B) TYPE: amino acid
         (C) STRANDEDNESS: single
         (D) TOPOLOGY: Not Relevant (ii) MOLECULE TYPE: peptide (iii) HYPOTHETICAL: NO (v) FRAGMENT TYPE: internal (xi) SEQUENCE DESCRIPTION: SEQ ID NO:1:

Glu Glu Arg Ala Asp Leu Ile Ala Tyr
1               5

(2) INFORMATION FOR SEQ ID NO:2:

(i) SEQUENCE CHARACTERISTICS:
         (A) LENGTH: 11 amino acids
         (B) TYPE: amino acid
         (C) STRANDEDNESS: single
         (D) TOPOLOGY: Not Relevant (ii) MOLECULE TYPE: peptide (iii) HYPOTHETICAL: NO (v) FRAGMENT TYPE: internal (xi) SEQUENCE DESCRIPTION: SEQ ID NO:2:

Thr Gly Pro Asn Leu His Gly Leu Phe Gly Arg
1               5                   10

(2) INFORMATION FOR SEQ ID NO:3:

(i) SEQUENCE CHARACTERISTICS:
         (A) LENGTH: 14 amino acids
         (B) TYPE: amino acid
         (C) STRANDEDNESS: single
         (D) TOPOLOGY: Not Relevant (ii) MOLECULE TYPE: peptide (iii) HYPOTHETICAL: NO (v) FRAGMENT TYPE: internal (xi) SEQUENCE DESCRIPTION: SEQ ID NO:3:

Thr Gly Gln Ala Pro Gly Tyr Ser Tyr Thr Ala Ala Asn Lys
1               5                   10

(2) INFORMATION FOR SEQ ID NO:4:

(i) SEQUENCE CHARACTERISTICS:
         (A) LENGTH: 6 amino acids
         (B) TYPE: amino acid
         (C) STRANDEDNESS: single
         (D) TOPOLOGY: Not Relevant (ii) MOLECULE TYPE: peptide (iii) HYPOTHETICAL: NO
```

(v) FRAGMENT TYPE: internal (xi) SEQUENCE DESCRIPTION: SEQ ID NO:4:

Tyr Ile Pro Gly Thr Lys
1               5

(2) INFORMATION FOR SEQ ID NO:5:

(i) SEQUENCE CHARACTERISTICS:
           (A) LENGTH: 13 amino acids
           (B) TYPE: amino acid
           (C) STRANDEDNESS: single
           (D) TOPOLOGY: Not Relevant (ii) MOLECULE TYPE: peptide (iii) HYPOTHETICAL: NO (v) FRAGMENT TYPE: internal (ix) FEATURE:
           (A) NAME/KEY: Modified-site
           (B) LOCATION: 1..13
           (D) OTHER INFORMATION: /note= "X at positions 1 and 4 were
               not identified in analysis of amino acid sequence."

(xi) SEQUENCE DESCRIPTION: SEQ ID NO:5:

Xaa Ile Ile Xaa Gly Glu Asp Thr Leu Met Glu Tyr Leu
1               5                   10

(2) INFORMATION FOR SEQ ID NO:6:

(i) SEQUENCE CHARACTERISTICS:
           (A) LENGTH: 5 amino acids
           (B) TYPE: amino acid
           (C) STRANDEDNESS: single
           (D) TOPOLOGY: Not Relevant (ii) MOLECULE TYPE: peptide (iii) HYPOTHETICAL: NO (v) FRAGMENT TYPE: internal (xi) SEQUENCE DESCRIPTION: SEQ ID NO:6:

Ile Phe Ile Met Lys
1               5

(2) INFORMATION FOR SEQ ID NO:7:

(i) SEQUENCE CHARACTERISTICS:
           (A) LENGTH: 5 amino acids
           (B) TYPE: amino acid
           (C) STRANDEDNESS: single
           (D) TOPOLOGY: Not Relevant (ii) MOLECULE TYPE: peptide (iii) HYPOTHETICAL: NO (v) FRAGMENT TYPE: internal (xi) SEQUENCE DESCRIPTION: SEQ ID NO:7:

Thr Gly Pro Asn Leu
1               5